(12) United States Patent
Harding et al.

(10) Patent No.: US 8,337,483 B2
(45) Date of Patent: Dec. 25, 2012

(54) VASCULAR ACCESS DEVICE CHAMBER REPLACEMENT

(75) Inventors: Weston F. Harding, Lehi, UT (US); Dinesh S. Kommireddy, Tarrytown, NY (US); Mark A. Crawford, Sandy, UT (US); S. Ray Isaacson, Roy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 383 days.

(21) Appl. No.: 11/931,483

(22) Filed: Oct. 31, 2007

(65) Prior Publication Data
US 2008/0215004 A1  Sep. 4, 2008

Related U.S. Application Data

(60) Provisional application No. 60/864,109, filed on Nov. 2, 2006.

(51) Int. Cl.
*A61M 39/06* (2006.01)
*A61M 1/00* (2006.01)

(52) U.S. Cl. .......................... 604/533; 604/122; 604/125

(58) Field of Classification Search .................. 604/122, 604/125, 244, 246, 249, 256, 265, 283, 533
See application file for complete search history.

(56) References Cited

U.S. PATENT DOCUMENTS

| | | |
|---|---|---|
| 4,324,239 A | 4/1982 | Gordon et al. |
| 4,765,588 A | 8/1988 | Atkinson |
| 4,834,720 A | 5/1989 | Blinkhorn |
| 5,251,873 A | 10/1993 | Atkinson et al. |
| 5,295,657 A | 3/1994 | Atkinson |
| 5,295,658 A | 3/1994 | Atkinson et al. |
| 5,342,316 A | 8/1994 | Wallace |
| 5,441,487 A | 8/1995 | Vedder |
| 5,474,544 A | 12/1995 | Lynn |
| 5,501,426 A | 3/1996 | Atkinson et al. |
| 5,520,665 A * | 5/1996 | Fleetwood ..................... 604/537 |
| 5,533,708 A | 7/1996 | Atkinson et al. |
| 5,549,651 A | 8/1996 | Lynn |
| 5,730,418 A * | 3/1998 | Feith et al. .................. 251/149.6 |
| 5,738,663 A | 4/1998 | Lopez |
| 5,957,898 A | 9/1999 | Jepson et al. |
| 6,171,287 B1 | 1/2001 | Lynn et al. |
| 6,261,282 B1 | 7/2001 | Jepson et al. |
| 6,344,033 B1 | 2/2002 | Jepson et al. |
| 6,428,520 B1 * | 8/2002 | Lopez et al. .................. 604/249 |
| 6,482,188 B1 * | 11/2002 | Rogers et al. ................. 604/249 |
| 6,595,964 B2 | 7/2003 | Finley et al. |
| 6,635,044 B2 | 10/2003 | Lopez |
| 6,651,956 B2 | 11/2003 | Miller |
| 6,669,681 B2 | 12/2003 | Jepson et al. |

(Continued)

FOREIGN PATENT DOCUMENTS
WO  WO 98/26835  6/1998

*Primary Examiner* — Victoria P Shumate
(74) *Attorney, Agent, or Firm* — Jeanne Lukasavage; Craig Metcalf; Kirton McConkie

(57) ABSTRACT

A vascular access device may include a body, housing, neck, and a septum with a substantially non-gaseous cross section. A method of operating a septum of a vascular access device may include providing a vascular access device in an external environment and actuating the septum without transferring a substantial amount of gas from within the device to the external environment of the device.

17 Claims, 8 Drawing Sheets

U.S. PATENT DOCUMENTS

| | | |
|---|---|---|
| 6,866,656 B2 | 3/2005 | Tingey et al. |
| 6,908,459 B2 | 6/2005 | Harding et al. |
| 7,056,316 B1 | 6/2006 | Burbank et al. |
| 7,306,199 B2 * | 12/2007 | Leinsing et al. ........... 251/149.6 |
| 2002/0193752 A1 | 12/2002 | Lynn |
| 2004/0073171 A1 | 4/2004 | Rogers et al. |
| 2004/0199126 A1 | 10/2004 | Harding et al. |
| 2005/0256500 A1 | 11/2005 | Fujii |
| 2006/0149305 A1 | 7/2006 | Cuevas et al. |
| 2006/0206061 A1 * | 9/2006 | Lopez et al. .................. 604/246 |
| 2007/0038189 A1 * | 2/2007 | Bartholomew ............... 604/249 |
| 2008/0172003 A1 * | 7/2008 | Plishka et al. ................ 604/249 |

* cited by examiner

VASCULAR ACCESS DEVICE CHAMBER REPLACEMENT

RELATED APPLICATIONS

This application claims the benefit of U.S. Provisional Application No. 60/864,109, filed Nov. 2, 2006, entitled VASCULAR ACCESS DEVICE CHAMBER REPLACEMENT, which is incorporated herein by reference.

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously.

The vascular access device commonly includes a Luer adapter to which other medical devices may be attached. For example, an administration set may be attached to a vascular access device at one end and an intravenous (IV) bag at the other. The administration set is a fluid conduit for the continuous infusion of fluids and pharmaceuticals. Commonly, an IV access device is a vascular access device that may be attached to another vascular access device, closes the vascular access device, and allows for intermittent infusion or injection of fluids and pharmaceuticals. An IV access device may include a housing and a septum for closing the system. The septum may be opened with a blunt cannula or a male Luer of a medical device.

When the septum of a vascular access device fails to operate properly, certain complications may occur. Complications associated with infusion therapy may cause significant morbidity and even mortality. One significant complication is catheter related blood stream infection (CRBSI). An estimate of 250,000-400,000 cases of central venous catheter (CVC) associated BSIs occur annually in US hospitals. Attributable mortality is an estimated 12%-25% for each infection and a cost to the health care system of $25,000-$56,000 per episode.

Current vascular access devices prevent complications, such as infection resulting in CRBSIs, by providing a septum that functions properly during attachment and/or access of the vascular access device by other medical devices. Septa that function properly will act, in part, as infection barriers between the internal and external environments of the vascular access device during attachment and/or access by other medical devices. By functioning properly as infection barriers, septa minimize CRBSI's and other complications. Thus, what are needed are various additional septa and related structures and methods capable of maximizing proper septum functionality.

BRIEF SUMMARY OF THE INVENTION

The present invention has been developed in response to problems and needs in the art that have not yet been fully resolved by currently available vascular access systems, devices, and methods. Thus, these systems, devices, and methods are developed to reduce complications, such as the risk and occurrence of CRBSIs, by providing septa and related structures and methods that maximize proper septum functionality.

A medical device may include a vascular access device having a body, a neck including a convex inner surface, and a septum housed partially within the convex inner surface of the neck. The septum may include two opposing slit surfaces, the neck may be secured to the body, and the neck and the septum may form a substantially non-gaseous cross section.

In one embodiment, the portion of the septum that is housed within the neck includes at least two different materials. In another embodiment, the at least two different materials include a first silicon and a second silicon. In another embodiment, the at least two different materials include a silicon and a foam elastomer.

In another embodiment, the septum is formed of a low durometer material that is capable of separating with minimal force and without exchanging gas, or any substantial amount of gas, with an external environment of the vascular access device. In another embodiment, the neck may form a convex section of the body. In this embodiment, the vascular access device may include a liquid housed between the convex surface of the neck and the two opposing slit surfaces of the septum. In this embodiment, the vascular access device may also include a concave inner surface of the body and a cavity formed within the concave surface of the body. The septum may also include a barrier between the neck and the cavity, and the barrier may include at least one channel capable of shuttling the fluid from between the convex surface of the neck and the two opposing slit surfaces of the septum, through the at least one channel, to the cavity.

In an alternate embodiment where the neck forms a convex section of the body, the vascular access device may also include a rigid structure that is housed between the convex surface of the neck and the two opposing slit surfaces of the septum. In this embodiment, the vascular access device may also include a concave inner surface of the body and a cavity formed within the concave surface of the body. The rigid structure may be capable of moving from between the convex surface of the neck and the two opposing slit surfaces of the septum into the cavity as the two opposing slit surfaces of the septum come into contact with the convex surface of the neck. In any embodiment including a rigid structure, a spring, such as a compression spring may be in contact with the rigid structure, and the force of the spring may bias the rigid structure from the cavity towards the neck.

A method of operating a septum of a vascular access device may include providing a vascular access device in an external environment and actuating the septum of the vascular access device without transferring a substantial amount of gas from within the device to the external environment of the device. The vascular access device may include a body, a neck secured or otherwise attached to or a part of the body, and a septum partially housed within the neck.

The device may also include a rigid member that is at least partially housed within the neck, and the method may also include transferring the rigid member from the neck to a location within the body. The device may also include a liquid that is at least partially housed within the neck, and the method may also include transferring the liquid from the neck to a location within the body. The septum may also include two opposing slit surfaces, and the method may also include separating the two opposing slit surfaces of the septum in two opposing lateral directions. In any of the previous methods, the neck may form a convex cross section of the body.

A medical device may include a means for accessing the vascular system of a patient that includes a septum, and a means for actuating the septum without transferring a substantial amount of gas from within the means for accessing the vascular system of a patient to an environment that is external to the means for accessing the vascular system of a patient. The means for actuating the septum may include a spring-loaded rigid structure, a liquid, and/or multiple materials within the septum.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
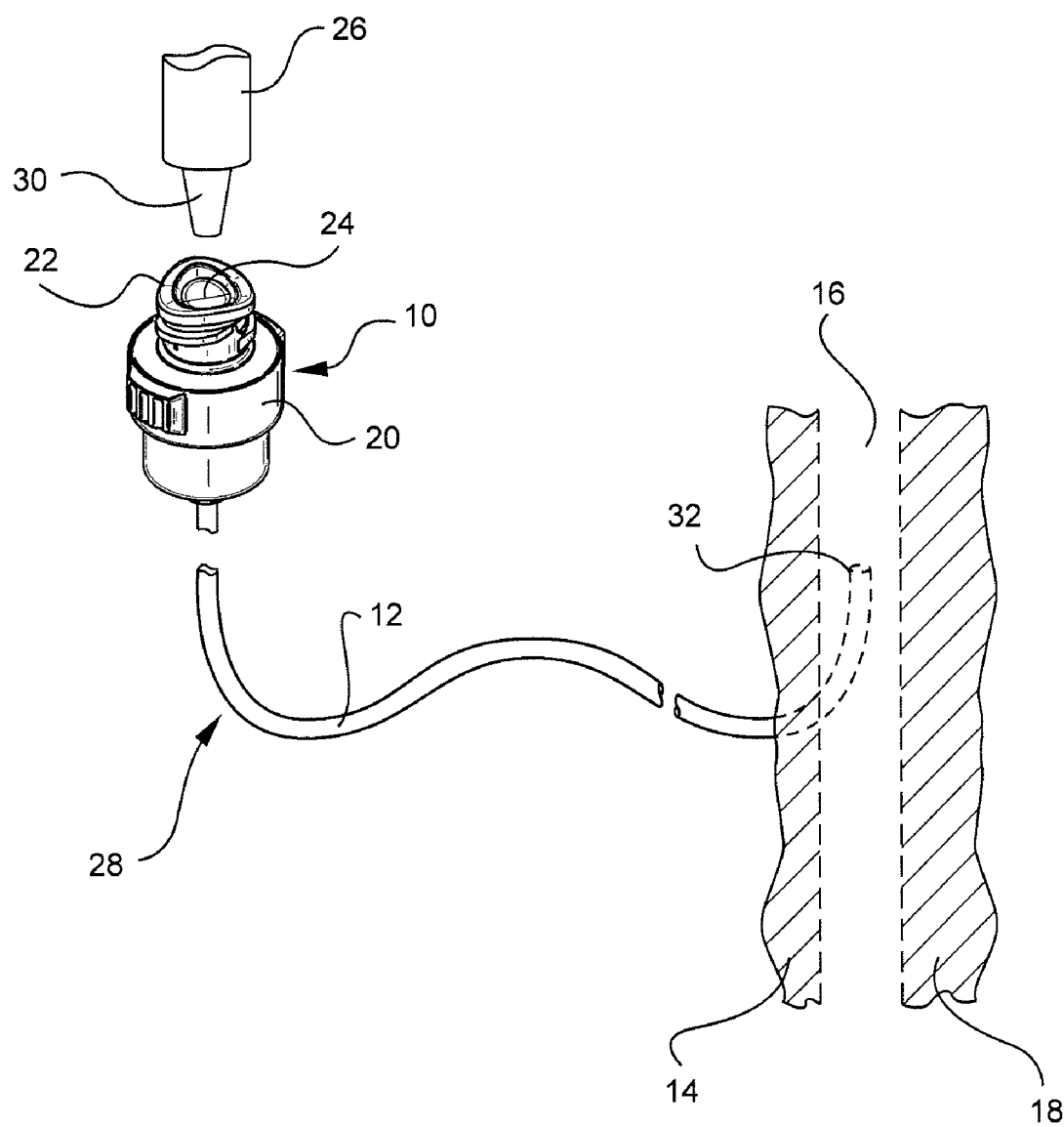
FIG. 1 is a perspective view of an extravascular system connected to the vascular system of a patient.

Referring now to FIG. 1, a vascular access device (also referred to as an extravascular device, intravenous access device, access port, and/or any device attached to or functioning with an extravascular system) 10 is used to introduce a substance via a catheter 12 across the skin 14 and into a blood vessel 16 of a patient 18. The vascular access device 10 includes a body 20 with a lumen and a septum 22 placed within the lumen. The septum 22 has a slit 24 through which a separate extravascular device 26, such as a syringe, may introduce a substance into the vascular access device 10.

The device 10 and all structures used in combination therewith may form a larger extravascular system 28. As part of the system 28, a tip 30 of the separate device 26 may be inserted into the device 10 through the slit 24 of the septum 22. The tip 30 will serve to communicate fluid through the device 10 and the end 32 of the catheter 12 when the device 10 is in use. In an embodiment of the invention, as the tip 30 penetrates the device 10, the two opposing slit 24 surfaces of the septum 22 will separate in opposing lateral directions and will stretch the slit 24 surfaces of the septum 22 in an axial direction, thus increasing the overall height of the septum 22. In this particular embodiment, as the height of the septum is increased, the seal between the device 10 and the tip 30 is rendered more effective.

Figure 2:
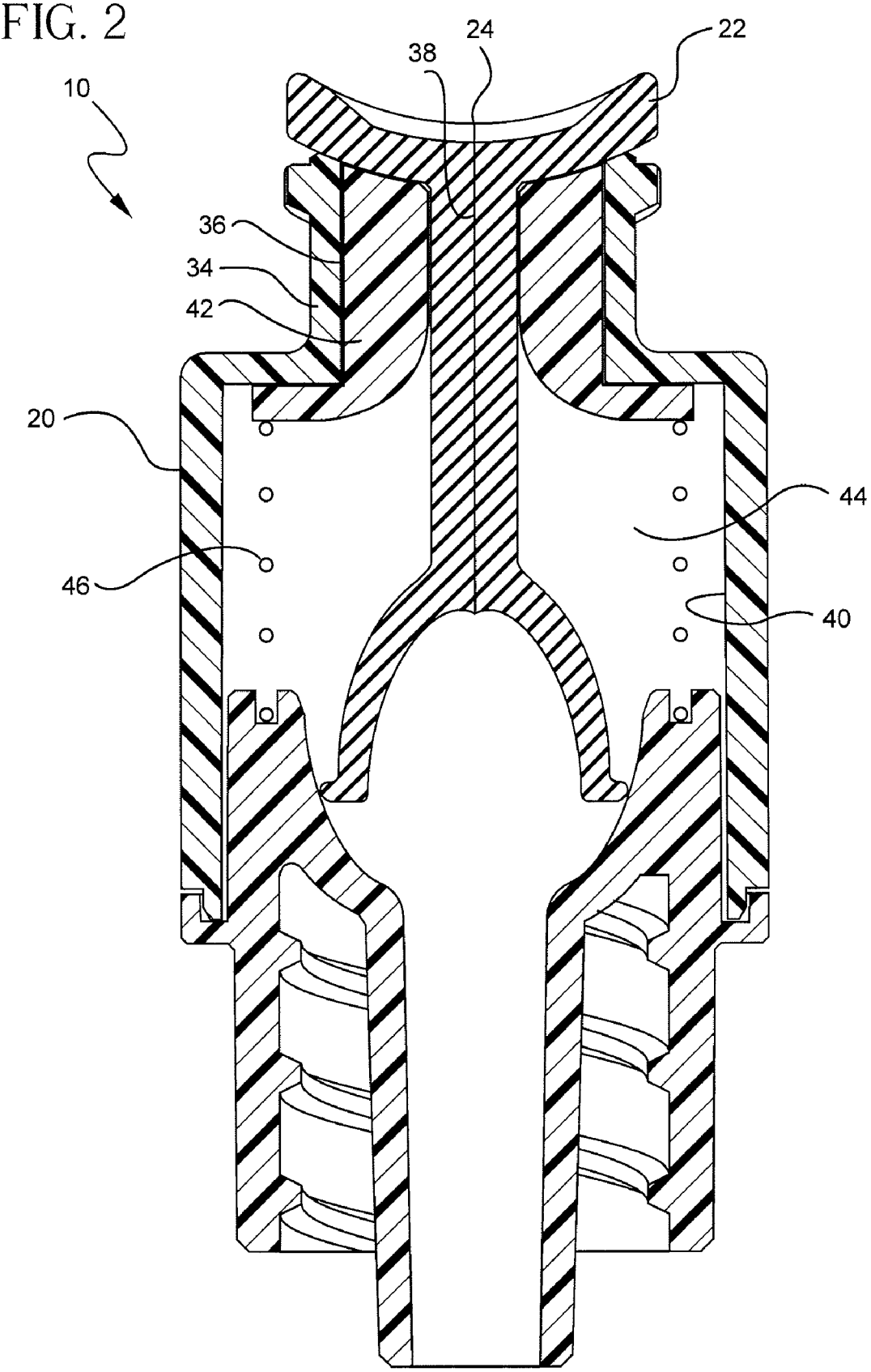
FIG. 2 is a cross section view of a vascular access device with a rigid structure.

Referring now to FIG. 2, a vascular access device 10 includes a body 20 forming a neck 34 along an upper portion of the body 20. The neck 34 includes a convex inner surface 36 along its length. The device 10 also includes a septum 22 that is partially housed within the convex inner surface 36 of the neck 34. The septum 22 includes two opposing slit surfaces 38 along the slit 24 of the septum 22. The neck 34 is secured to the body 20 as a section of the body 20. The body 20 may also include a concave inner surface 40 along a lower portion of the body 20. The concave inner surface 40 is concave in relation to the convex inner surface 36 of the neck 34, and the convex inner surface 36 is convex in relation to the concave inner surface 40 of the body.

The neck 34 and septum 22 form a substantially non-gaseous cross section. Along the substantially non-gaseous cross section, a rigid structure 42 may be contained within the body 20, between the body 20 and the septum 22. The rigid structure 42 is capable of moving between the convex inner surface 36 of the neck 34 and the two opposing slit surfaces 38 of the septum 22 into the cavity 44 housed within the inner concave surface 40 of the body. The rigid structure 42 will move into the cavity 44 as the septum 22 comes into contact with the convex inner surface 36 of the neck 34. A compression spring 46 is in contact with the rigid structure 42 such that the force of the spring 46 biases the rigid structure 42 from the cavity 44 towards the neck 34.

Figure 3:
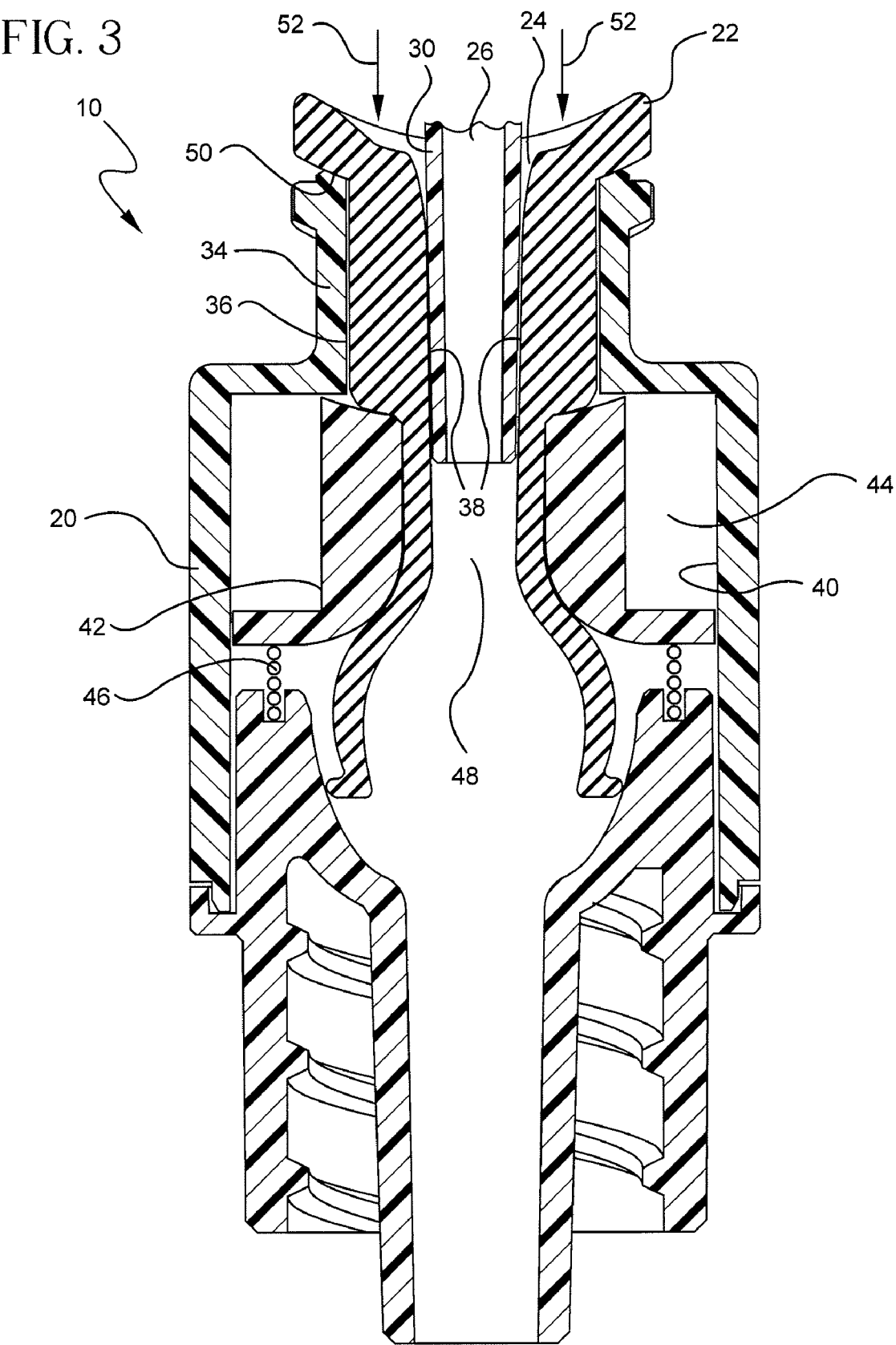
FIG. 3 is a cross section view of the vascular access device of FIG. 2 engaged with the tip of a separate access device.

Referring now to FIG. 3, the vascular access device 10 of FIG. 2 is shown with the tip 30 of a separate access device 26 inserted into the septum 22 of the device 10. As the tip 30 is inserted into the septum 22, the two opposing slit surfaces 38 are forced in opposing lateral directions towards the body 20 of the device 10. Simultaneously, the rigid structure 42 is forced against the compression spring 46 from the neck 34 towards and into the cavity 44, providing an open fluid path 48 through which fluid may be communicated with the tip 30.

The septum 22 is adhered or otherwise secured to the top portion of the body at point 50 along the diameter of the neck 34 of the body 20. The septum 22 is adhered or otherwise secured or fixed to a top surface of the neck 34 of the body.

The portion of the septum 22 adhered or otherwise secured or fixed to a top surface of the neck 34 of the body can extend out of an upper opening in the neck and be fixed to an exterior surface of the body, as shown. Because the septum 22 is secured to the body 20, as the tip 30 is inserted into the slit 24 of the septum 22, the friction caused by the tip 30 rubbing against the two opposing slit surfaces 38 will force the septum 22 to stretch in an axial direction 52, causing the overall length of septum 22 to increase. As the overall length of the septum 22 increases, it will provide a longer and more effective seal against the outer surface of the tip 30.

The embodiments described with reference to FIGS. 2 and 3 thus provide a vascular access device with an improved septum and sealing mechanism. A method of operating the septum 22 of the device 10 of FIGS. 2 and 3 includes providing the device 10 in an external environment and actuating the septum 22 without transferring a substantial amount of gas from within the device 10 to the external environment of the device 10. The device 10 includes a rigid member 42 at least partially housed within the neck 34. The method may further include transferring the rigid member 42, or spring-loaded rigid structure, from within the neck 34 to another location within the body 20, such as the cavity 44.

Figure 4:
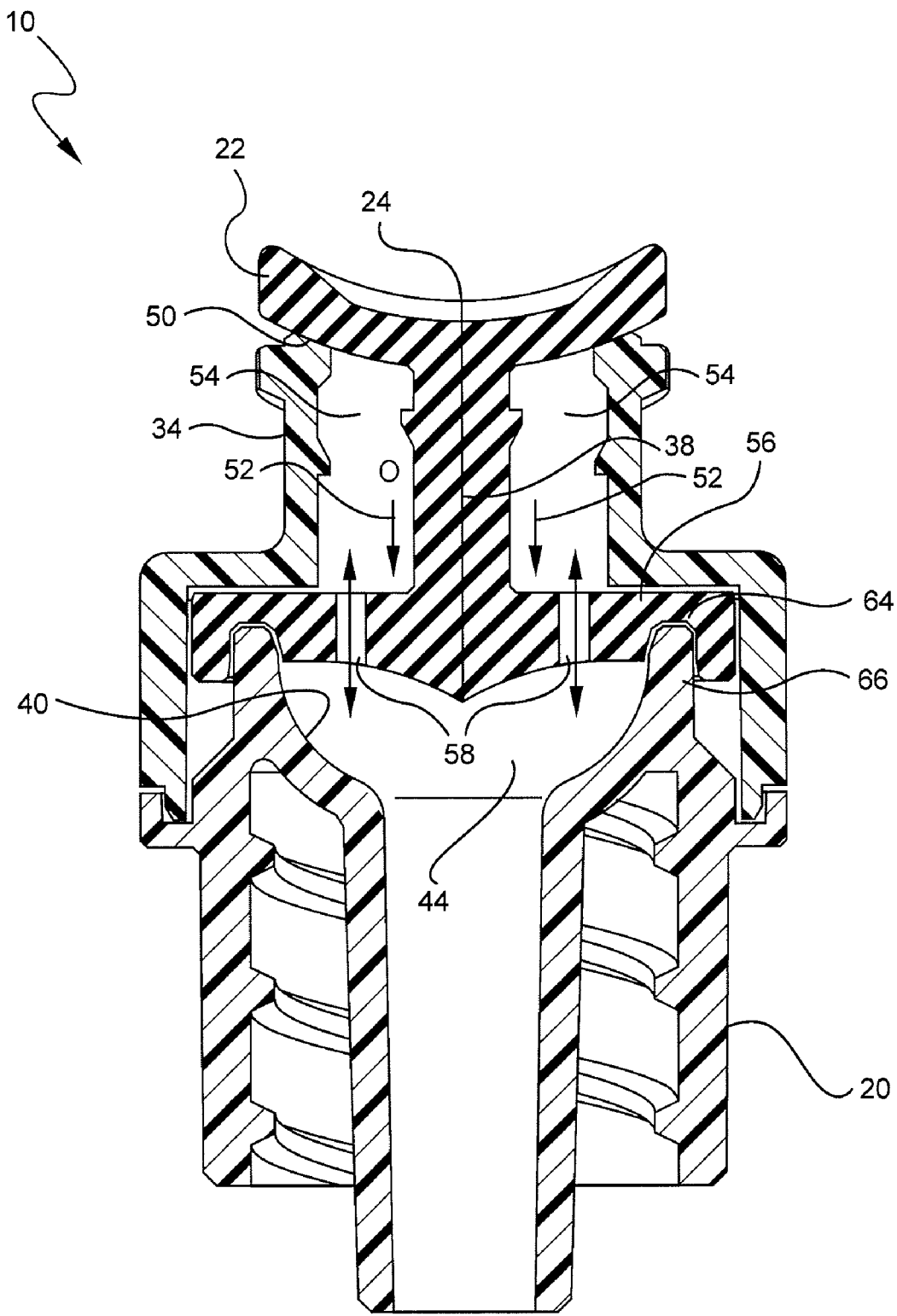
FIG. 4 is a cross section view of a vascular access device with a septum having at least one fluid channel.

Referring now to FIG. 4, a vascular access device 10 includes a body 20, a neck 34 secured to an upper portion of the body 20, a convex inner surface 36 of the neck 34, and a septum 22 housed partially within the convex inner surface of the neck 34. The septum 22 includes two opposing slit surfaces 38 within the slit 24. The neck 34, septum 22, and fluid filled area 54 form a substantially non-gaseous cross section of the device 10. The device 10 also includes a concave inner surface 40 of the body 20. The concave inner surface 40 forms a cavity 44 within the device 10. The septum 22 further includes a barrier 56 at the floor of the septum 22 between the neck 34 and cavity 44. The barrier 56 includes at least one channel 58 capable of shuttling fluid from between the convex inner surface 36 of the neck 34 and the two opposing slit surfaces 38 of the septum 22, through the at least one channel 58, to the cavity 44. Thus, the liquid that is housed in the liquid area 54 between the convex inner surface 36 of the neck 34 and the two opposing slit surfaces 38 of the septum 22 may communicate freely with the fluid in the cavity 44 by being shuttled through the at least one channel 58.

In use, the device 10 described with reference to FIG. 4 permits the fluid or liquid at least partially housed within the neck 34 to be transferred from within the neck 34 to another location within the body 20 of the device 10. Thus, as the tip 30 of a separate access device 26 is inserted into the septum 22, the space used up by the tip 30 within the neck 34 will cause the chamber housing the liquid 54 to expel the liquid 54 through the at least one channel 58 and into the cavity 44. Since the septum 22 is secured at a point 50 along the diameter of the body 20 of the device 10, as the tip 30 is inserted into the septum, the two opposing slit surfaces 38 of the septum 22 will separate in opposing lateral directions toward the inner convex surface 36 of the neck 34, and the septum 22 will stretch in an axial direction 52, causing the overall length of the septum 22 to increase.

Figure 5:
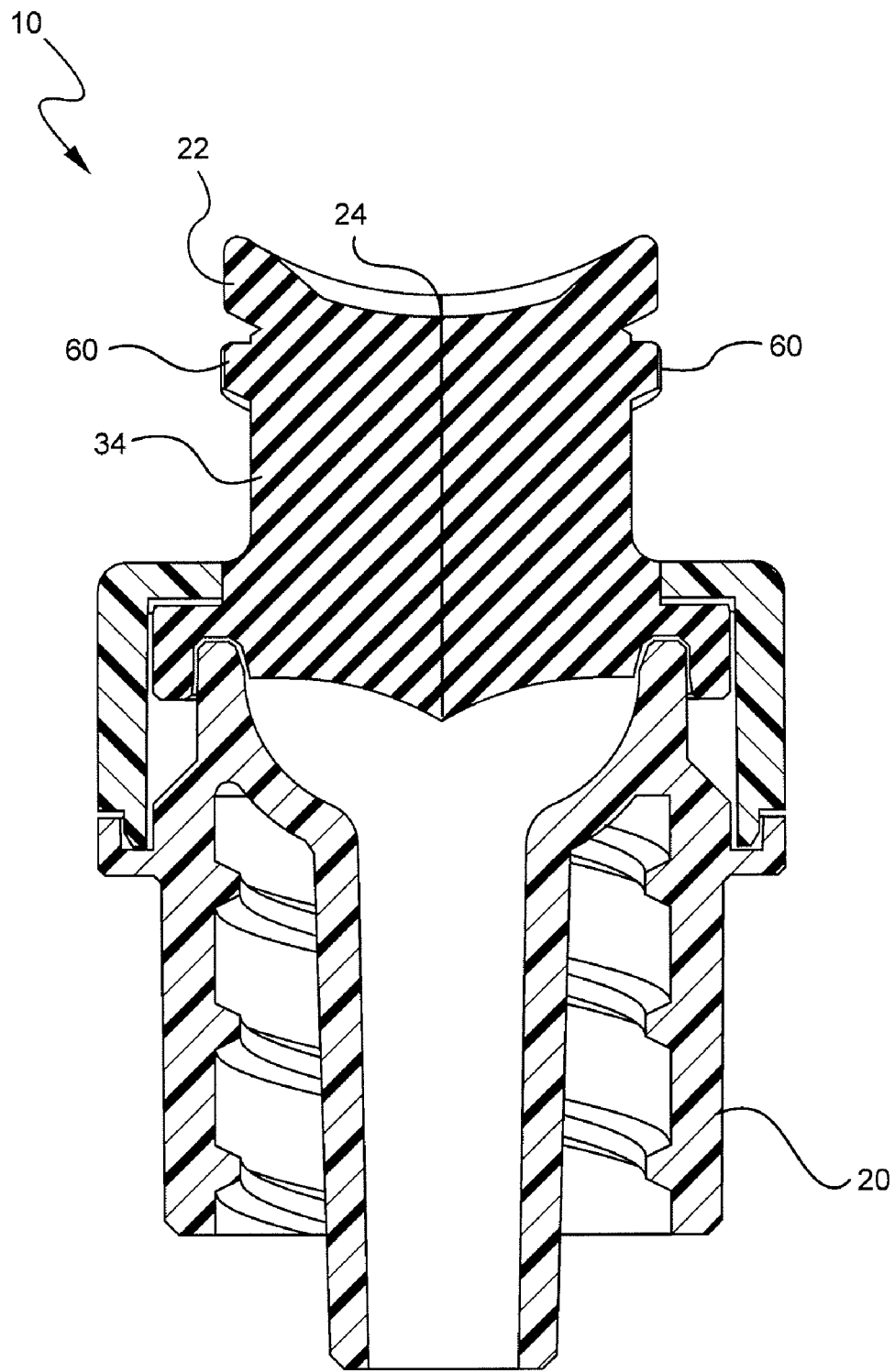
FIG. 5 is a cross section view of a vascular access device with a septum forming the neck of the device.

Referring now to FIG. 5, a vascular access device 10 includes a body 20 and a neck 34 secured to the body 20. A septum 22 resides, or is housed within the neck 34. The septum 22 is formed of a resilient or elastomeric material such as silicon. The septum may also be made from any low durometer material, such as foam, that is capable of separating along the slit 24 of the septum 22 as the tip 30 of a separate access device 26 is inserted in the slit 24. The septum 22 may form the entire neck 34 of the body 20 of the device 10, and may include threads 60 capable of securing the neck 34 of the device 10 to a separate access device 26.

Figure 6:
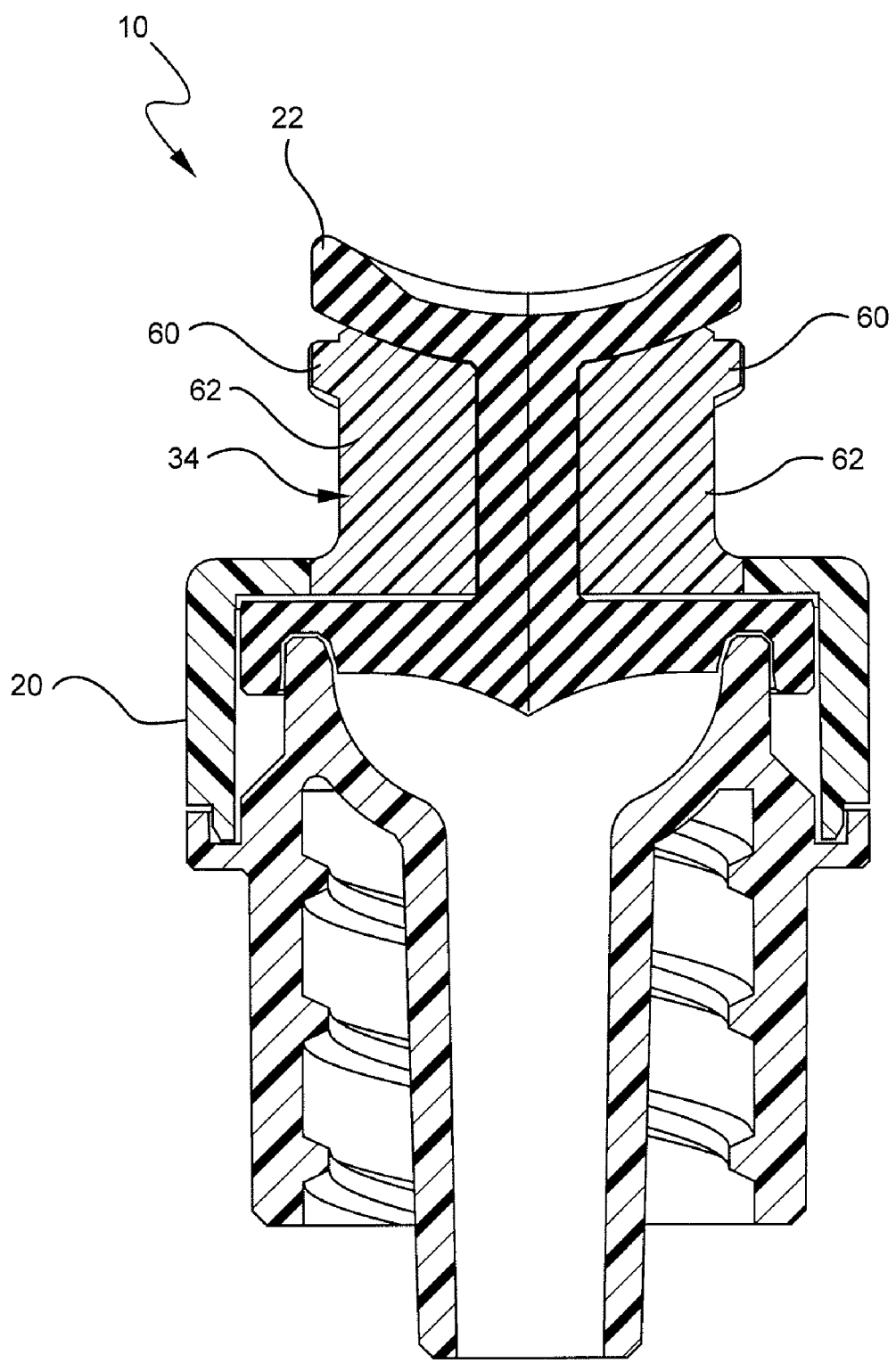
FIG. 6 is a cross section view of a vascular access device having two resilient materials forming the neck of the device.

Referring now to FIG. 6, a vascular access device 10 includes a body 20 and a neck 34 secured and attached to the body 20. The neck 34 may include a septum 22 formed of a first resilient material, such as a first silicon, and a structure and a material 62 supporting the septum 22 and formed of a second resilient material, such as a second silicon. Supporting structure 62 includes threads 60, which may mate with the threads of a separate access device 26. The materials of the septum 22 and supporting structure 62 may be varied to provide any two different materials, including silicons, foam, and other elastomers.

Figure 7:
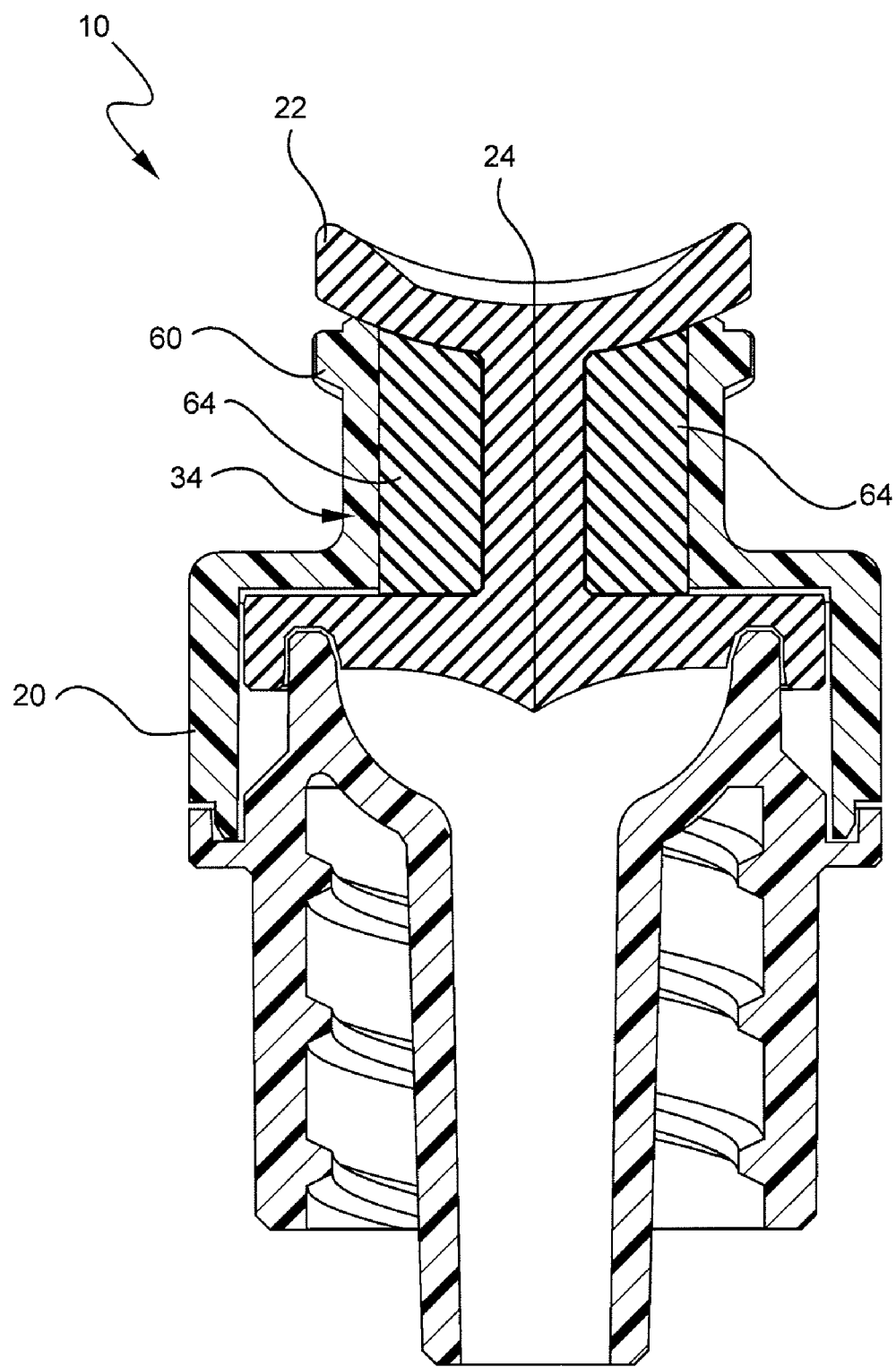
FIG. 7 is a cross section view of the vascular access device with a neck, a septum, and a resilient material between the neck and the septum.

Referring now to FIG. 7, a vascular access device 10 includes a body 20 secured or otherwise attached to a neck 34 in the upper portion of the body 20. The neck 34 is formed of a hardened material such as a polycarbonate material. Within the neck 34, a resilient septum 22 is housed along with a second intermediate elastomeric material 64 that is housed between the septum 22 and the neck 34. The elastomeric material 64 may be an elastomeric foam material, such as a material with a durometer capable of changing shape without significant force exerted from the tip 30 of a separate access device 26 that is inserted into the slit 24 of the septum 22. The elastomeric material 64 and resilient material of the septum 22 will change shape and flex as the tip 30 is inserted into the slit 24 without creating any vacuum or transfer of air within or across the materials of the septum 22 and elastomeric material 64.

Figure 8:
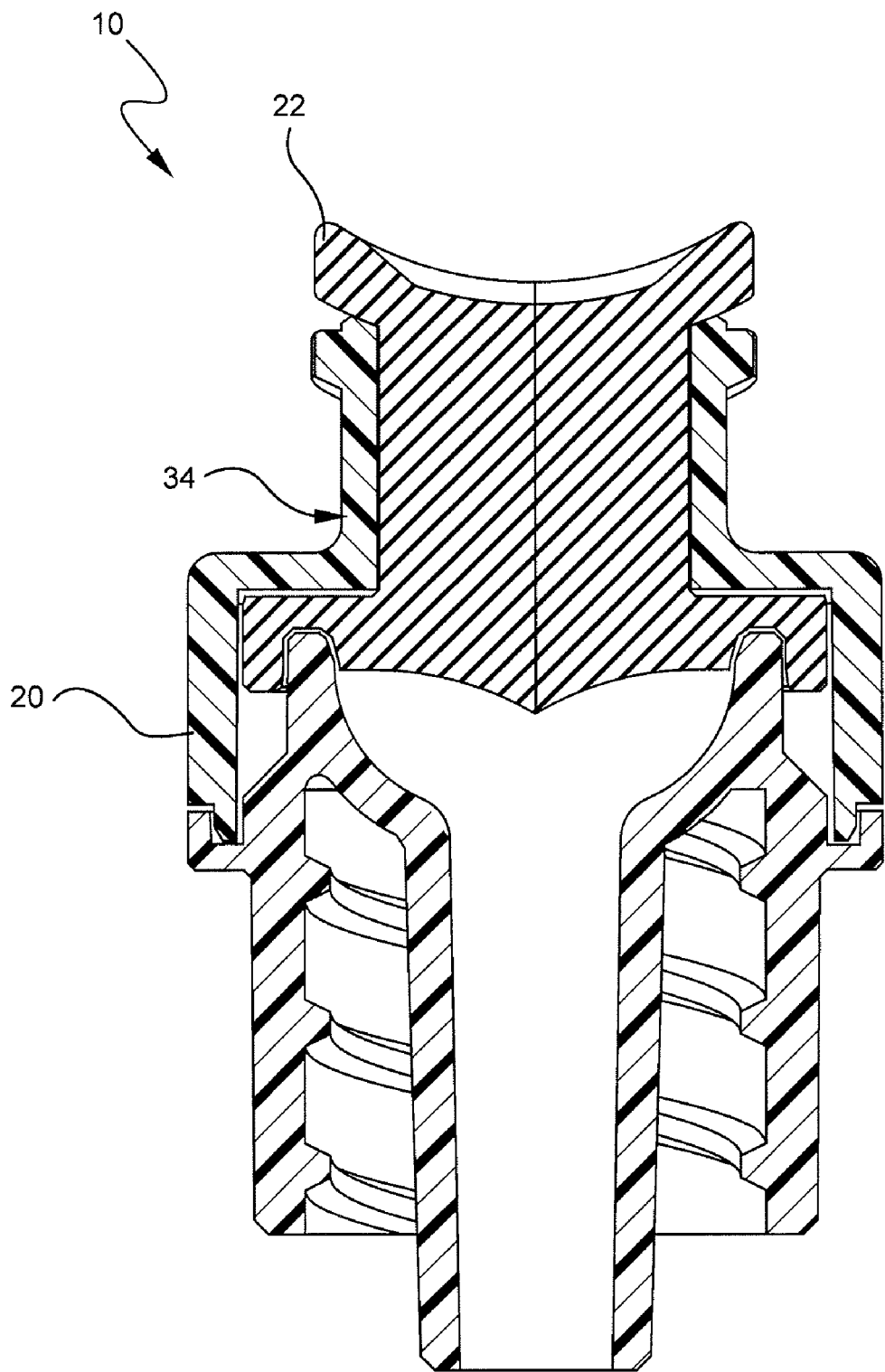
FIG. 8 is a cross section view of a vascular access device with a neck and a septum partially housed within the neck.

Referring now to FIG. 8, a vascular access device 10 includes a body 20 attached or otherwise secured to a neck 34 along a top portion of the body 20. The neck 34 at least partially houses a septum 22 which fills the entire inner lumen of the neck 34. The neck 34 and body 20 are formed of a hardened material such as a polycarbonate and the septum 22 is formed of any elastomeric material such as silicon or a material with a low durometer that will change shape with minimal force and without creating a vacuum upon removal of an inserted tip 30 of a separate access device 26.

The resilient materials of the embodiments described with reference to FIGS. 5 through 8 that are capable of changing shape upon insertion and removal of a tip 30, will preferably return to their original state upon removal of the tip 30. For all of the elastomeric materials of the embodiments described with reference to FIGS. 5 through 8, a tip 30 may be inserted into the septa 22 with minimal force and without exchanging gas, or any significant amount of gas, with an external environment of the vascular access device 10. Thus, the septa 22 of FIGS. 5 through 8 provide a convenient, hermetic seal between the internal fluid exchange of the devices 10 and the potentially non-sterile surrounding external environment of the device 10.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical device, comprising:
a vascular access device including a body having a neck portion and a lower portion that defines a cavity, the neck portion having a smaller cross-sectional area than the lower portion;

a septum housed partially within the neck portion, a portion of the septum extending out of an upper opening in the neck portion and being fixed to an exterior surface of the body, wherein the septum includes two opposing slit surfaces;

a rigid structure positioned within the neck portion and at least partially encompassing the septum, the rigid member being movable from within the neck portion and into the cavity portion when the vascular access device is accessed by a separate extravascular device.

2. The medical device of claim 1, further comprising a spring in contact with the rigid structure, wherein the force of the spring biases the rigid structure from the cavity towards the neck portion.

3. The medical device of claim 1, wherein the two opposing slit surfaces of the septum are in contact along a portion of the septum when the septum is in a closed position.

4. The medical device of claim 3, wherein the rigid structure at least partially encompasses the portion of the septum having the two opposing slit surfaces of the septum in contact when the septum is in a closed position.

5. The medical device of claim 1, wherein a bottom portion of the septum contacts an inner surface of the cavity.

6. The medical device of claim 1, wherein the neck portion has a length between a top and bottom of the neck, and the rigid structure has a length between the top and bottom of the rigid structure, the length of the neck portion being approximately equal to or greater the length of the rigid structure.

7. The medical device of claim 1, wherein the neck portion further includes a top surface, and the septum being secured to the top surface of the neck portion.

8. A medical device, comprising:
a vascular access device including a body having a neck portion and a lower portion that defines a cavity, the neck portion having a smaller cross-sectional area than the lower portion;

a septum housed at least partially within the neck portion, a portion of the septum extending out of an upper opening in the neck portion and being fixed to an exterior surface of a top portion of the body, the septum comprising two opposing slit surfaces housed partially within the neck portion;

a rigid structure disposed intermediate between an inner surface of the neck portion and the septum and at least partially encompassing the septum;

wherein the rigid structure is movable from between the inner surface of the neck portion and the two opposing surfaces of the septum into the cavity.

9. The medical device of claim 8 further comprising a spring in contact with the rigid structure, said spring biasing the rigid structure from the cavity toward the neck portion.

10. The medical device of claim 8 wherein when the vascular access device is accessed by a separate access device, the two opposing slit surfaces are forced in opposing lateral directions toward the body of the device.

11. The medical device of claim 10 wherein when the vascular access device is accessed by a separate access device the rigid structure is forced against the spring and into the cavity.

12. The medical device of claim 10 wherein when the vascular access device is accessed by a separate access device an open fluid path through the device is formed.

13. The medical device of claim 8, wherein the two opposing slit surfaces of the septum are in contact along a portion of the septum when the septum is in a closed position.

14. The medical device of claim 13, wherein the rigid structure at least partially encompasses the portion of the septum having two opposing slit surfaces of the septum in contact when the septum is in a closed position.

15. The medical device of claim 8, wherein the portion of the septum is fixed to an exterior surface of a top portion of the body.

16. A medical device, comprising:
a vascular access device including a body having an inner surface, a cavity formed within the inner surface of the body, and a neck portion having an inner surface;

a septum housed partially within neck portion, a portion of the septum extending out of the neck portion and being fixed to an exterior surface of the body, wherein the septum includes two opposing slit surfaces;

a rigid structure housed between the inner surface of the neck and the septum and at least partially encompassing the septum;

wherein the rigid structure is capable of moving from between the inner surface of the neck and the septum into the cavity of the body when the vascular access device is accessed by a separate extravascular device; and a spring in contact with the rigid structure and the inner surface of the cavity, the spring biasing the rigid structure from the cavity toward the neck.

17. The medical device of claim 16, wherein the neck, the rigid structure, and septum form a cross section in which the opposing slit surfaces are in contact.

* * * * *